United States Patent
Ohsawa

(10) Patent No.: US 6,422,870 B1
(45) Date of Patent: Jul. 23, 2002

(54) PREFERENCE DETECTING APPARATUS AND METHOD AND MEDIUM THEREFOR

(75) Inventor: Eiichi Ohsawa, Saitama (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/575,520

(22) Filed: May 22, 2000

(30) Foreign Application Priority Data

May 26, 1999 (JP) ............................................ 11-146025

(51) Int. Cl.[7] ............................................... G09B 19/00
(52) U.S. Cl. ...................................................... 434/236
(58) Field of Search ................................ 434/236, 350, 434/353

(56) References Cited

U.S. PATENT DOCUMENTS

| | | | | |
|---|---|---|---|---|
| 4,789,235 A | * | 12/1988 | Borah et al. ............ | 351/246 X |
| 5,243,517 A | * | 9/1993 | Schmidt et al. ......... | 600/544 X |
| 5,945,988 A | * | 8/1999 | Williams et al. ........ | 345/327 X |
| 6,058,367 A | * | 5/2000 | Sutcliffe et sal. .......... | 705/1 X |
| 6,075,971 A | * | 6/2000 | Williams et al. ......... | 455/5.1 X |
| 6,099,319 A | * | 8/2000 | Zaltman et al. .......... | 434/236 X |
| 6,159,015 A | * | 12/2000 | Buffington et al. ......... | 434/236 |
| 6,164,975 A | * | 12/2000 | Weingarden et al. ... | 434/322 X |
| 6,330,592 B1 | * | 11/2001 | Makuch et al. ......... | 709/217 X |

* cited by examiner

*Primary Examiner*—Joe H. Cheng
*Assistant Examiner*—Chanda Harris
(74) *Attorney, Agent, or Firm*—Bell, Boyd & Lloyd LLC

(57) ABSTRACT

A preference detecting apparatus causes a test subject to play a game displayed on a display unit. Images of arbitrary objects are displayed at arbitrary timings on different display units surrounding the display unit for displaying the game. Since the test subject plays the game displayed on the display unit, time pressure is applied on the test subject. Accordingly, arbitrariness is eliminated, and an object image on which the test subject initially focused the attention is determined as a preference.

13 Claims, 18 Drawing Sheets

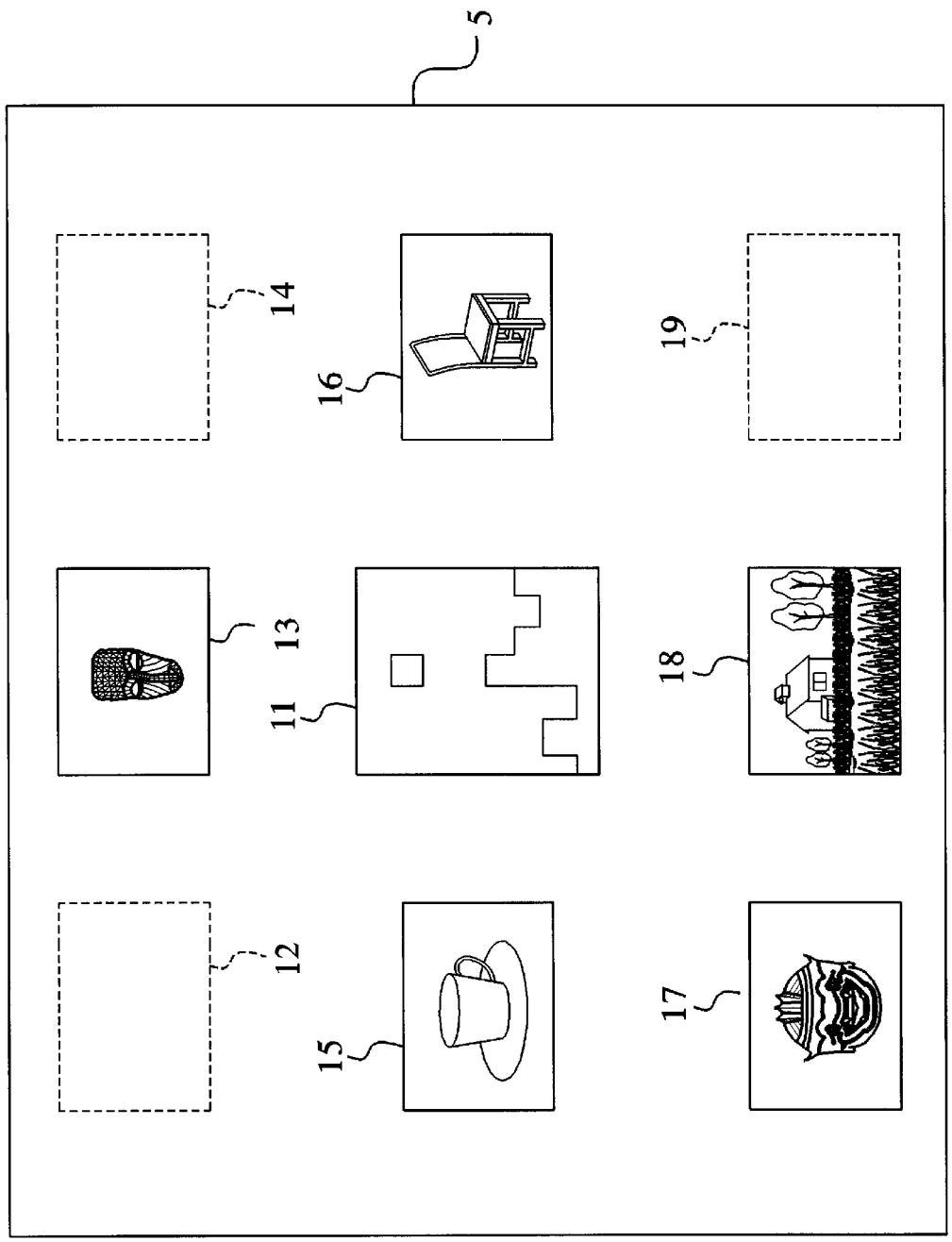

PREFERENCE DETECTING APPARATUS AND METHOD AND MEDIUM THEREFOR

BACKGROUND OF THE INVENTION

1. Field of the Invention

The present invention relates to preference detecting apparatuses and methods and media therefor. More particularly, the present invention relates to a preference detecting apparatus and method and a medium therefor in which a preference of a test subject is rapidly and accurately detected by applying pressure in the form of time (hereinafter referred to as "time pressure") on the test subject, thus eliminating arbitrariness in the test subject.

2. Description of the Related Art

People's interest varies depending on each person. By detecting a preference of a person, it is possible to provide the person with information that may be of interest to the person. Various methods have been proposed to detect a person's preference.

A first method is to make each person report their preference beforehand and to register the preference. A second method is to observe the behavior of each person for a long period of time and to determine their preference based on the observation result.

The first method of making each person report their preference and registering the preference involves difficulty in classifying preferred objects and in covering all the objects. Since the first method is based on the preference reported by each person, arbitrary preferences cannot be eliminated.

The second method of observing the behavior of each person makes it difficult to narrow down the preferences, and it requires a long period of time to finally determine the preference.

SUMMARY OF THE INVENTION

Accordingly, it is an object of the present invention to provide a preference detecting apparatus and method for rapidly and accurately determining a preference of a test subject while eliminating arbitrariness in the test subject.

A preference detecting apparatus according to an aspect of the present invention includes a providing unit for providing a test subject with predetermined information. A detecting unit detects the response of the test subject to the information provided by the providing unit. An applying unit applies time pressure on the response of the test subject to the information provided by the providing unit. A determining unit determines the preference of the test subject based on the detection result obtained by the detecting unit.

The providing unit may provide the test subject with images as the predetermined information.

The images may be classified by category.

The detecting unit may detect the response of the test subject based on focusing conditions of the test subject on the images.

The detecting unit may detect an image on which the test subject initially focused his attention.

The determining unit may determine the preference of the test subject based on ratios regarding the images, in which each ratio is obtained as the number of times the attention of the test subject was focused on each image to the number of times each image was displayed.

The determining unit may determine the preference of the test subject based on ratios regarding the images, in which each ratio is obtained as the number of times the initial attention of the test subject was focused on each image to the number of times each image was displayed.

The determining unit may determine the preference of the test subject based on a peak value of the ratios.

The determining unit may detect the peak value of the ratios by changing the time pressure applied by the applying unit.

The applying unit may include an executing unit for causing the test subject to execute a predetermined task and an adjusting unit for adjusting a period up to completion of the task.

The task may be a game.

According to another aspect of the present invention, a preference detecting method includes a providing step of providing a test subject with predetermined information. A detecting step detects the response of the test subject to the information provided by the providing step. An applying step applies time pressure on the response of the test subject to the information provided by the providing step. A determining step determines the preference of the test subject based on the detection result obtained by the detecting step.

According to another aspect of the present invention, there is provided a computer-readable medium for causing a computer to execute a program. The program includes a providing step of providing predetermined information to a test subject. A detecting step detects the response of the test subject to the information provided by the providing step. An applying step applies time pressure on the response of the test subject to the information provided by the providing step. A determining step determines the preference of the test subject based on the detection result obtained by the detecting step.

According to a preference detecting apparatus, a preference detecting method, and a computer-readable medium for causing a computer to execute a program, arbitrariness in a test subject can be eliminated, and accurate and rapid detection of the test subject's preference can be performed.

BRIEF DESCRIPTION OF THE DRAWINGS

FIG. 4 is an illustration of an example of a display of an image display unit shown in FIG. 1;

DESCRIPTION OF THE PREFERRED EMBODIMENT

Figure 1:
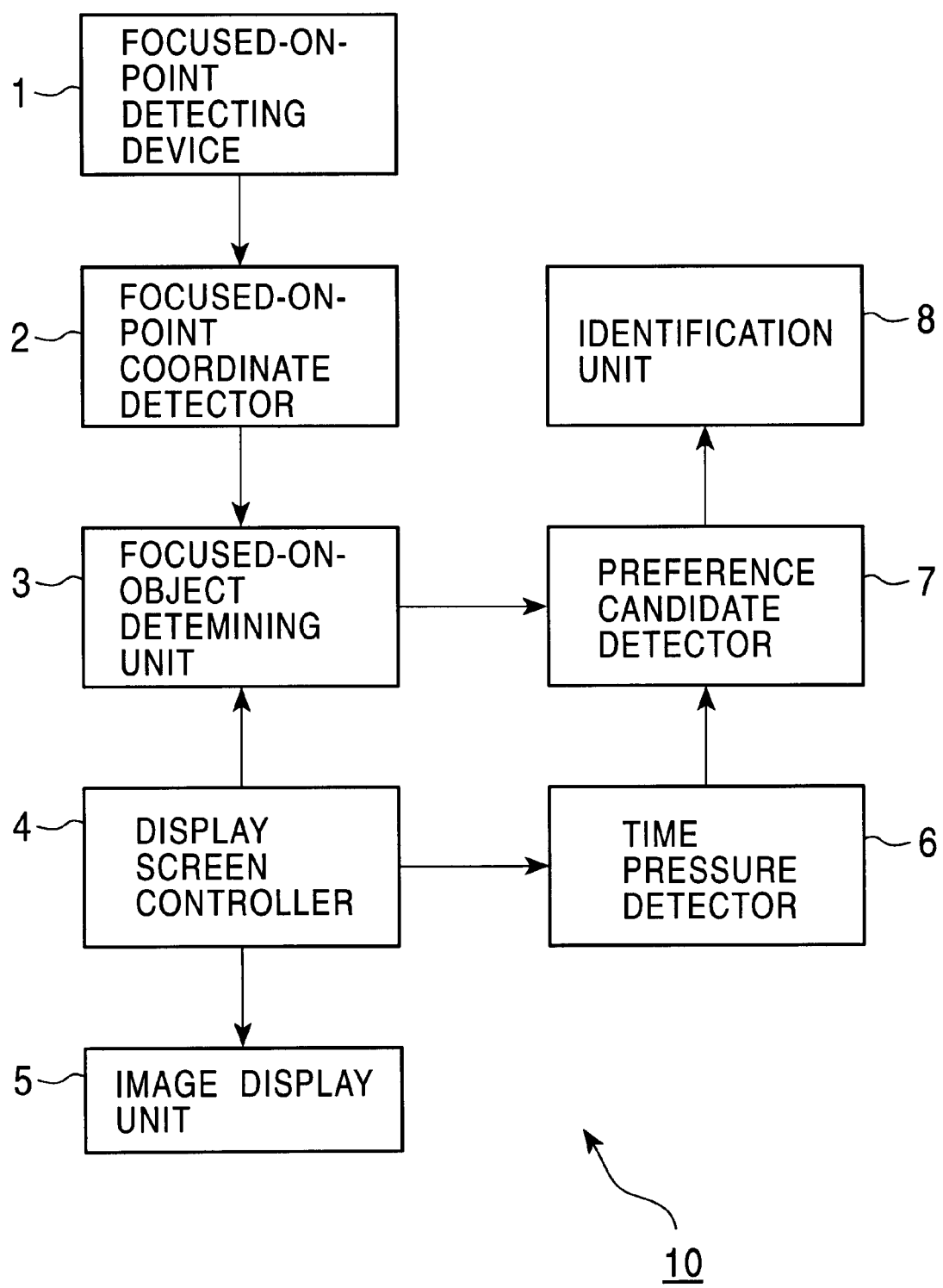
FIG. 1 is a block diagram of a preference detecting apparatus according to an embodiment of the present invention.

The present invention is described hereinafter with reference to the accompanying drawings. FIG. 1 shows the structure of a preference detecting apparatus 10 according to an embodiment of the present invention. Referring to FIG. 1, a focused-on-point detecting device 1 is, for example, an eye-mark recorder, and is mounted on the head of a test subject. The cornea of the test subject is scanned with infrared light, and light reflected therefrom is detected, thus determining the point (hereinafter referred to as a "focused-on-point") at which the attention of the test subject is directed. The eye-mark recorder is capable of detecting the focused-on-point at a frequency of, for example, 30 frames per second. It is known that humans redirect the eyes from one focused-on-point to another focused-on-point at 20 msec to 50 msec, and that the focused-on-point moves approximately five times per second at most. Hence, accurate and reliable detection of the focused-on-point of the test subject is made possible by detecting the focused-on-point at a frequency of 30 frames per second.

A focused-on-point coordinate detector 2 detects the coordinates of the focused-on-point based on the output from the focused-on-point detecting device 1, and outputs the detected focused-on-point coordinates to a focused-on-object determining unit 3. A display screen controller 4 outputs images of predetermined objects to an image display unit 5 formed on, for example, a cathode-ray tube (CRT) or a liquid crystal display (LCD), and the image display unit 5 displays the images. The display screen controller 4 outputs information about objects to be displayed on the image display unit 5 to the focused-on-object determining unit 3.

The focused-on-object determining unit 3 determines which object image the test subject is focusing on, based on the focused-on-point coordinates detected by the focused-on-point coordinate detector 2 and on the information about the object images which are supplied from the display screen controller 4 and are displayed on the image display unit 5. The focused-on-object determining unit 3 outputs the determination result to a preference candidate detector 7.

A time pressure detector 6 detects time pressure applied on the test subject based on a signal supplied from the display screen controller 4. The time pressure detector 6 outputs the detection result to the preference candidate detector 7.

The preference candidate detector 7 detects the test-subject's preference based on the determination result concerning the focused-on-object, which is supplied from the focused-on-object determining unit 3, and based on the time pressure when the test subject is focusing the attention on the focused-on-object, which is supplied from the time pressure detector 6. An identification unit 8 performs statistical processing of a preference candidate supplied from the preference candidate detector 7, and identifies the preference of the test subject.

The above components, i.e., the focused-on-point coordinate detector 2 to the identification unit 8, apart from the focused-on-point detecting device 1, can be formed by a personal computer.

Figure 2:
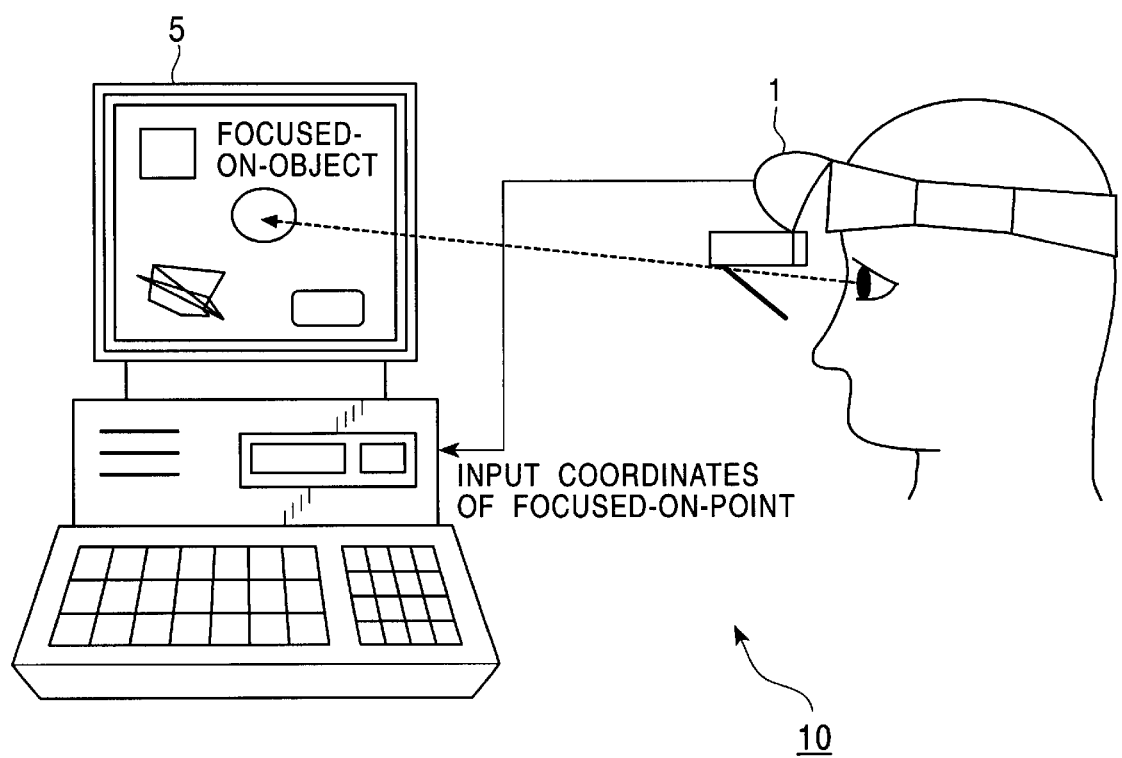
FIG. 2 is an illustration of a mode of use of the preference detecting apparatus of the present invention.

FIG. 2 schematically shows a mode of use of the preference detecting apparatus 10. As shown in FIG. 2, the focused-on-point detecting device 1 is mounted on the head of the test subject. The test subject plays a game while looking at an image displayed on the image display unit 5. Focused-on-point information detected by the focused-on-point detecting device 1 is supplied to the focused-on-point coordinate detector 2.

Figure 3:
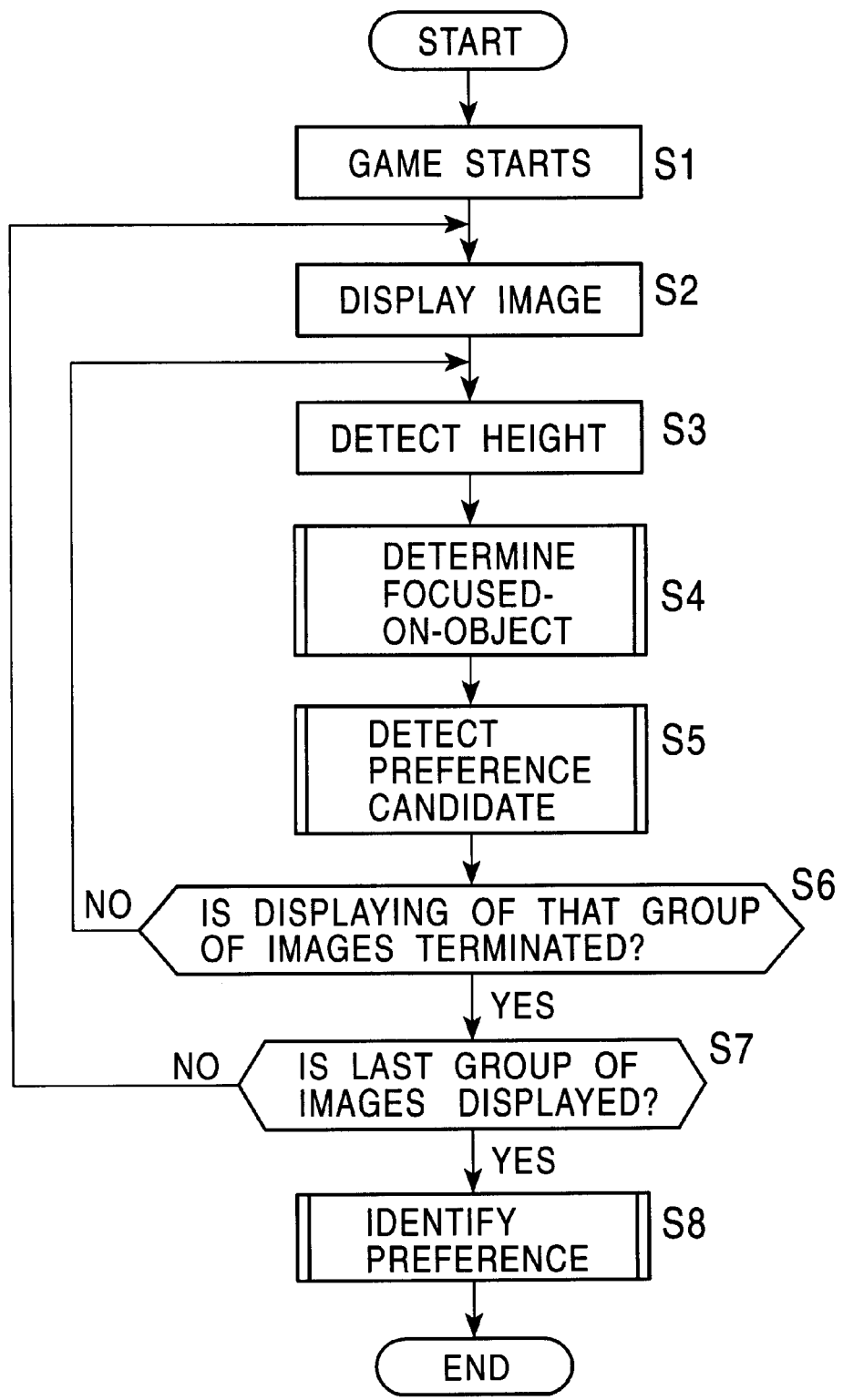
FIG. 3 is a flowchart showing a process performed by the preference detecting apparatus shown in FIG. 1.

FIG. 3 is a flowchart showing a process for detecting preference. In step S1, the display screen controller 4 displays the image of the game, and the test subject plays the game. In step S2, the display screen controller 4 displays images of predetermined objects on portions surrounding the image of the game.

FIG. 4 shows an example of a display of the image display unit 5. A display unit 11 at the center of the image display unit 5 displays the game image. Display units 12 to 19 surrounding the display unit 11 each display an image of a predetermined object.

FIGS. 5A to 5D to FIGS. 8A to 8D show examples of images of objects displayed on the display units 12 to 19. FIGS. 5A to 5D show images of objects 1 to 4 indicating inanimate objects. FIGS. 6A to 6D show images of objects 5 to 8 indicating animate objects. FIGS. 7A to 7D show images of objects 9 to 12 indicating masks. FIGS. 8A to 8D show images of objects 13 to 16 indicating landscapes. In this example, there are four object categories, i.e., inanimate objects, animate objects, masks, and landscapes. However, the object categories are not limited to these four types, and it is possible to appropriately prepare predetermined categories in accordance with the preference to be detected.

The image display unit 5 simultaneously displays a plurality of arbitrary images on the display units 12 to 19 for a predetermined period of time, such as for five seconds.

In step S3, the time pressure detector 6 detects time pressure based on a signal output from the display screen controller 4. Specifically, the time pressure is detected as the height H of a target block 51 in the game displayed on the display unit 11.

Figure 9:
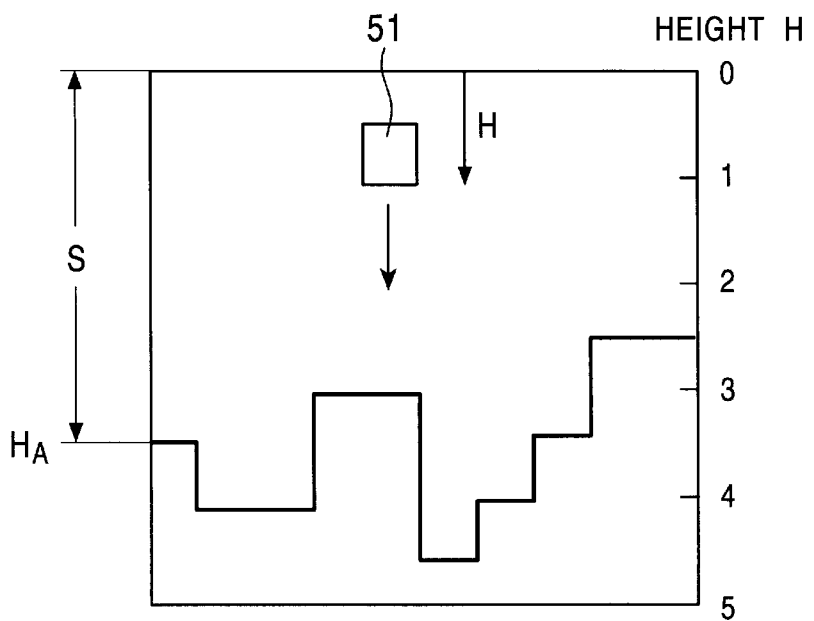
FIG. 9 is an illustration of an example of a display of a game.

In this example, the game displayed on the display unit 11 is Tetris (trademark). Referring now to FIG. 9, the target block 51 falls downward from the top, and the test subject plays the game by stacking the target block 51 at predetermined positions. The test subject is required to determine where to stack the target block 51 at the time the target block 51 appears, that is, when the height H of the target block 51 is the greatest. In FIG. 9, the highest position is indicated by "0", and the lowest position is indicated by "5". In other words, the target block 51 is at the highest position when the height H has the lowest value. When the test subject is determining the position to stack the target block 51, the greatest cognitive demand is applied on the test subject. Specifically, the greatest time pressure is applied on the test subject.

In contrast, when the target block 51 is at a lower position, it is likely that the test subject has determined the position to stack the target block 51. Hence, the time pressure applied on the test subject is low. Accordingly, the height H of the target block 51 indicates the time pressure applied on the test subject.

In step S4, the focused-on-object determining unit 3 determines an object (hereinafter referred to as a "focused-on-object") at which the attention of the test subject is directed. More specifically, the test subject is playing the game as a real-time task in which the visual perception load is great. During progression of the game, time urgency degree with respect to the achievement of the task varies. In this case, the time urgency degree is great when the target block 51 is at a high position, whereas the time emergency degree is small when the target block 51 is at a low position. Images of various objects, apart from the visual object relating to the task, i.e., the image of the game, are displayed at random within the visual field of the test subject. Basically, the test subject plays the game while looking at the image displayed on the display unit 11. When an image of an object apart from the visual object relating to the task suddenly appears, the test subject subconsciously responds to that stimulus and shifts the focused-on-point to that object. This physiological phenomenon is known as saccadic eye movement.

The focused-on-point detecting device 1, i.e., the eye-mark recorder, detects the movement of the eye of the test subject. The focused-on-point coordinate detector 2 detects the coordinates of the focused-on-point. The focused-on-object determining unit 3 determines the focused-on-point (focused-on-object) at which the attention of the test subject is directed at that time, based on the focused-on-point coordinates output from the focused-on-point coordinate detector 2 and on information about the images displayed on the image display unit 5, which are output from the display screen controller 4.

Figure 10:
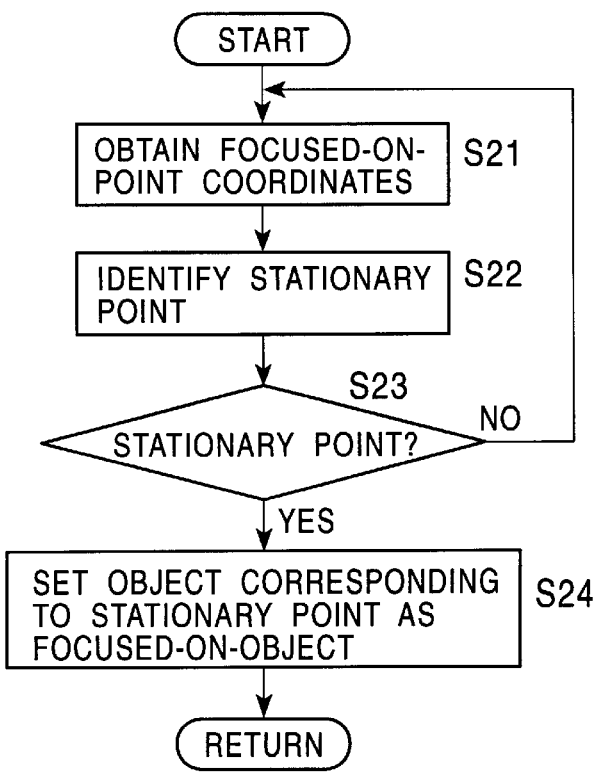
FIG. 10 is a flowchart showing details of step S4 in FIG. 3 for determining a focused-on-object.

FIG. 10 shows details of step S4 in FIG. 3 for determining the focused-on-object. In step S21, the focused-on-object determining unit 3 obtains the coordinates of the focused-on-point from the focused-on-point coordinate detector 2. In step S22, the focused-on-object determining unit 3 identifies a stationary point with respect to the obtained focused-on-point coordinates. More specifically, the focused-on-object determining unit 3 determines whether the focused-on-point coordinates are maintained unchanged over a predetermined period of time set in advance, within a predetermined area which is relatively small. In other words, the focused-on-object determining unit 3 determines whether the focused-on-point coordinates represent a stationary point. In step S23, if the focused-on-object determining unit 3 determines that the focused-on-point coordinates do not represent a stationary point, the focused-on-object determining unit 3 returns to step S21, and the process from step S21 onward is repeated. In step S23, if the focused-on-object determining unit 3 determines that the focused-on-point coordinates obtained in step S21 represent a stationary point, in step S24, the focused-on-object determining unit 3 compares the coordinates of a display position of each object supplied from the display screen controller 4 and the focused-on-point coordinates obtained in step S21, thus setting the object displayed at the position corresponding to the focused-on-point (stationary point) as a focused-on-object.

Figure 11:
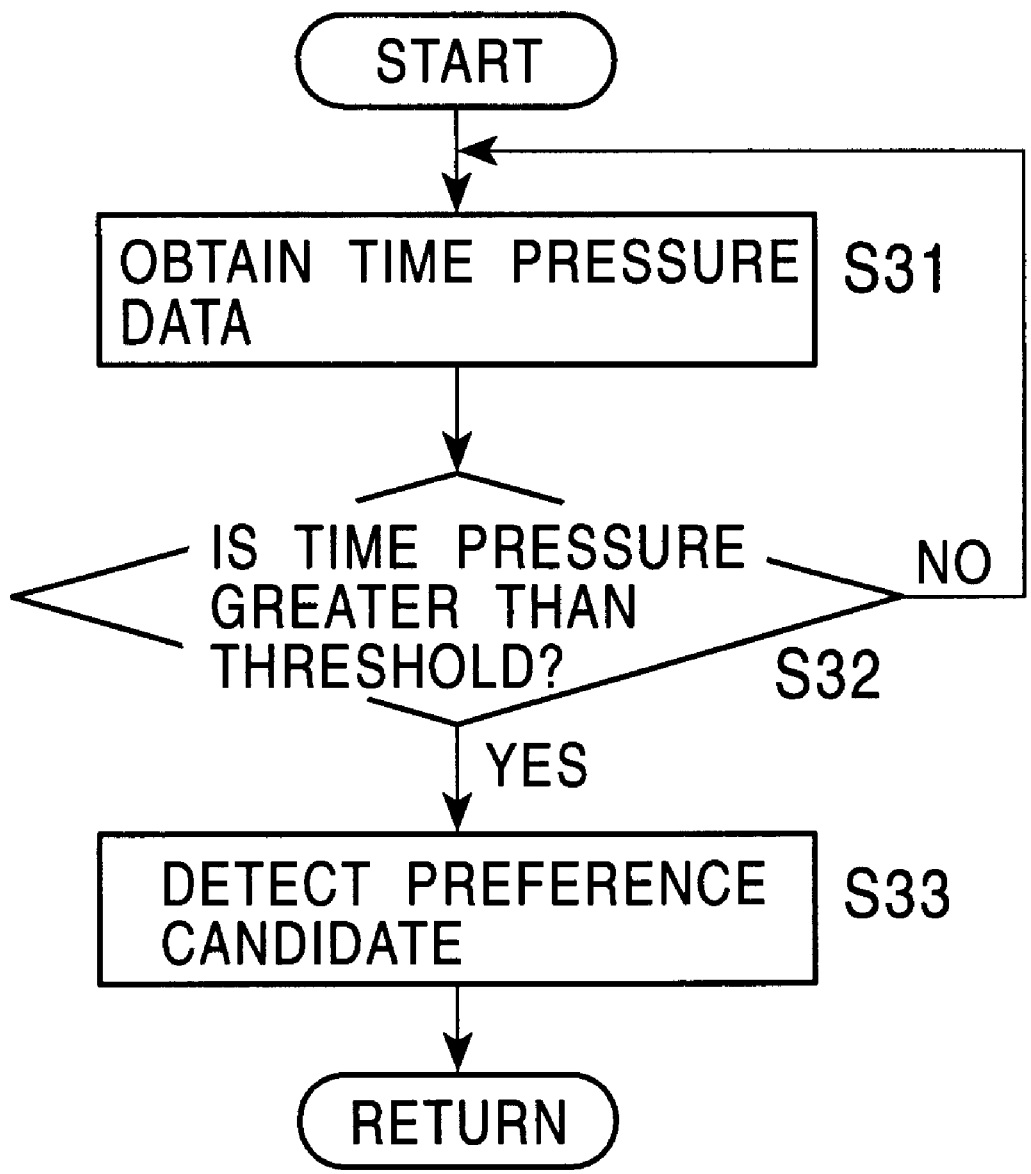
FIG. 11 is a flowchart showing details of step S5 in FIG. 3 for detecting a preference candidate.

Turning back to FIG. 3, after the focused-on-object has been set, the preference candidate detector 7 detects a preference candidate in step S5. FIG. 11 shows details of step S7 in FIG. 3.

Referring to FIG. 11, in step S31, the preference candidate detector 7 obtains time pressure data from the time pressure detector 6. In this example, the preference candidate detector 7 obtains the height data H of the target block 51. In step S32, the preference candidate detector 7 determines whether the value of the time pressure obtained in step S31 is greater than a predetermined threshold set in advance. In other words, the preference candidate detector 7 determines whether the height H is less than the predetermined threshold. If the time pressure at the time the test subject is directing the attention at the focused-on-object supplied from the focused-on-object determining unit 3 is smaller than the predetermined threshold, it is difficult to reliably detect the test subject's preference (the reason for this is described hereinafter). The preference candidate detector 7 returns to step S31, and the process from step S31 onward is repeated. In step S32, if it is determined that the time pressure is greater than the threshold, the preference candidate detector 7 detects the focused-on-object supplied from the focused-on-object determining unit 3 at that time as a preference candidate.

Referring again to FIG. 3, in step S6, the display screen controller 4 determines whether display of that group of object images has been terminated. In this case, the display screen controller 4 determines whether five seconds have passed since that group of images was started to be displayed. If it is determined that five seconds have not passed since the images of the objects were first displayed, the process returns to step S3, and the process from step S3 onward is repeated. If it is determined in step S6 that five seconds have passed since the images of the predetermined objects were first displayed on the image display unit 5, the display screen controller 4 determines in step S7 whether the last group of images to be displayed on the image display unit 5 has been displayed. If there is a group of images yet to be displayed, the process returns to step S2, and the process from step S2 onward is repeated. Specifically, arbitrary objects are displayed again for five seconds in a pattern differing from the previous displaying pattern, and a similar process is performed.

In step S7, if the process determines that the image of the last group of objects has been displayed, the identification unit 8 identifies the test subject's preference in step S8.

Figure 12:
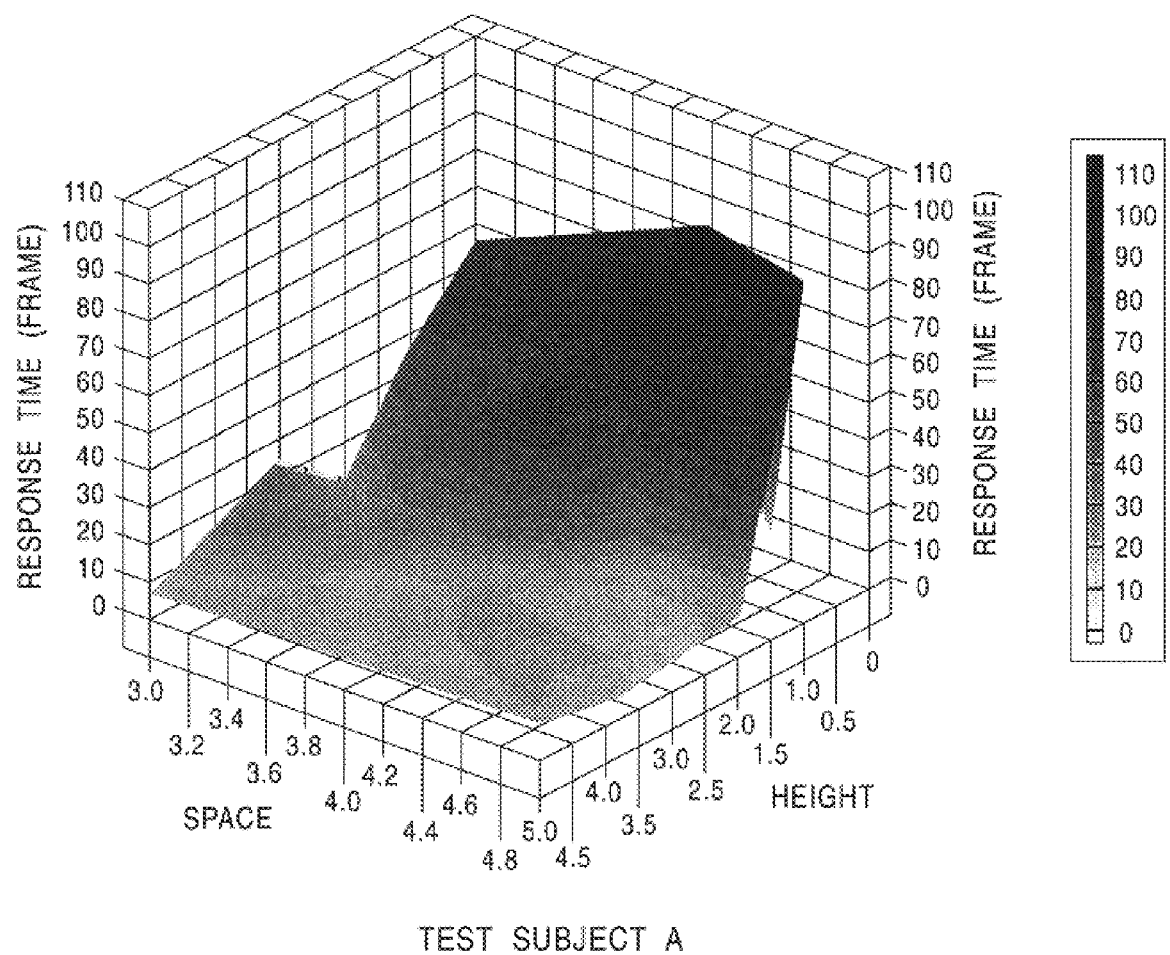
FIG. 12 is a graph showing average response times of a test subject A.

Before describing the identification processing performed by the identification unit 8, the relationship between the time pressure and average response times is described. FIG. 12 shows the relationship between the time pressure applied on the test subject A and the average response times, which was obtained experimentally. The vertical axis indicates the average response times between displaying of images which are not part of the game and the test subject's movement of the focused-on-point to each object. The horizontal axis represents the height H and space S (time pressure).

Figure 13:
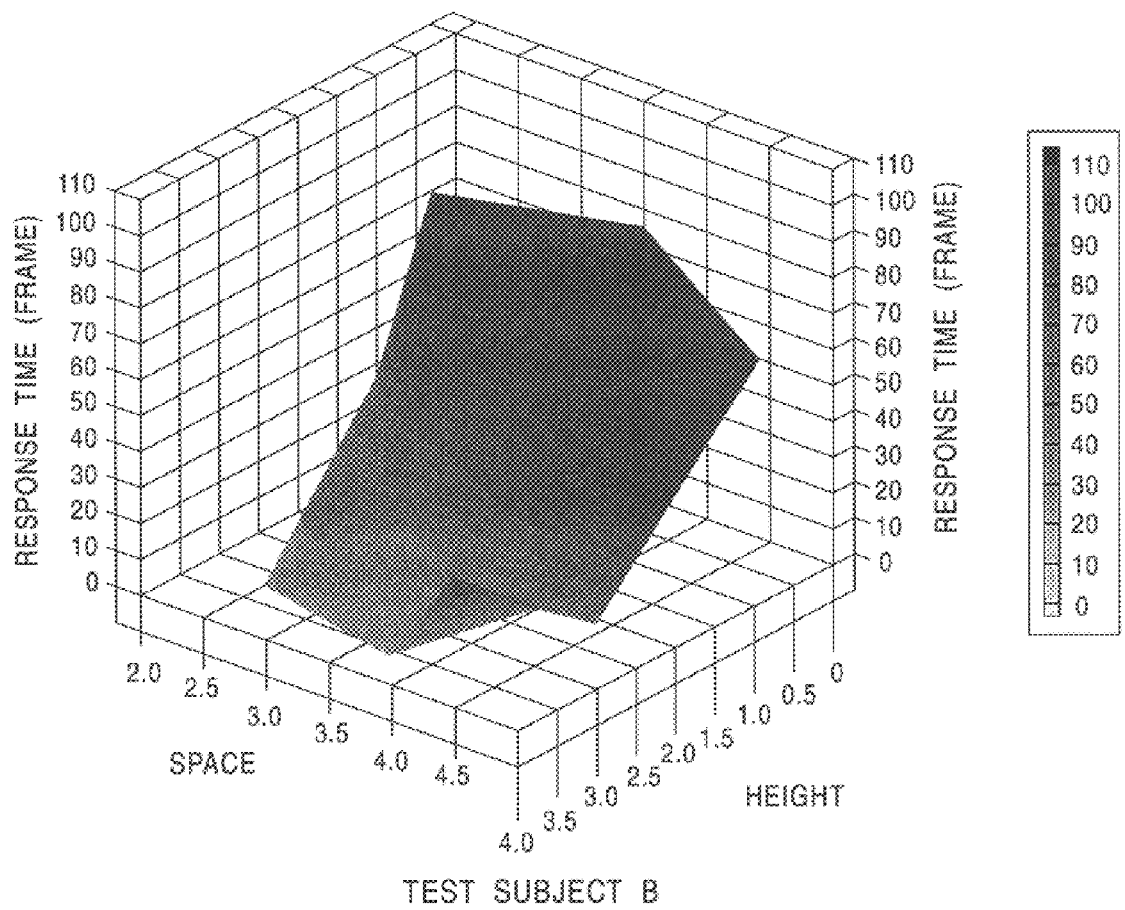
FIG. 13 is a graph showing average response times of a test subject B.

As shown in FIG. 9, the space S is represented by a distance between the uppermost position and the average height HA of stacked blocks. The greater the space S, the more time is allowed for the test subject to determine the position to stack the target block 51. In other words, when the space S is large, the time pressure applied on the test subject is low. In contrast, when the space S is small, the time allowed for the test subject to determine the position to stack the target block 51 is short. As a result, the time pressure is increased. FIG. 13 shows the relationship between the time pressure (the height H and the space S) applied on the test subject B and average response times, which was obtained experimentally.

As shown in FIGS. 12 and 13, both test subjects A and B have longer response times when the target block 51 is at a high position, that is, when the height H has a low value. This indicates that, when the target block 51 appears (when the target block 51 is at the highest position), the test subject is required to determine the position to stack the target block 51. At this time, the greatest cognitive demand is applied on the test subject. In other words, the greatest time pressure is applied on the test subject, and the response time to a stimulus unrelated to the task is prolonged. In contrast, when the target block 51 is at a low position (when the height H has a large value), the test subject has already determined where to stack the target block 51. Hence, the time pressure is decreased, and the response to the displayed image at that time is rapid.

With regard to the space factor, the larger the empty space in the upper region (i.e., the larger the space S), the shorter the average response time. In contrast, when the empty space is small (i.e., the smaller the space S), the time pressure is increased. In other words, the smaller the space S, the greater the time pressure. Accordingly, the response speed concerning the movement of the focused-on-point varies, depending on the magnitude of the time pressure.

Figure 14:
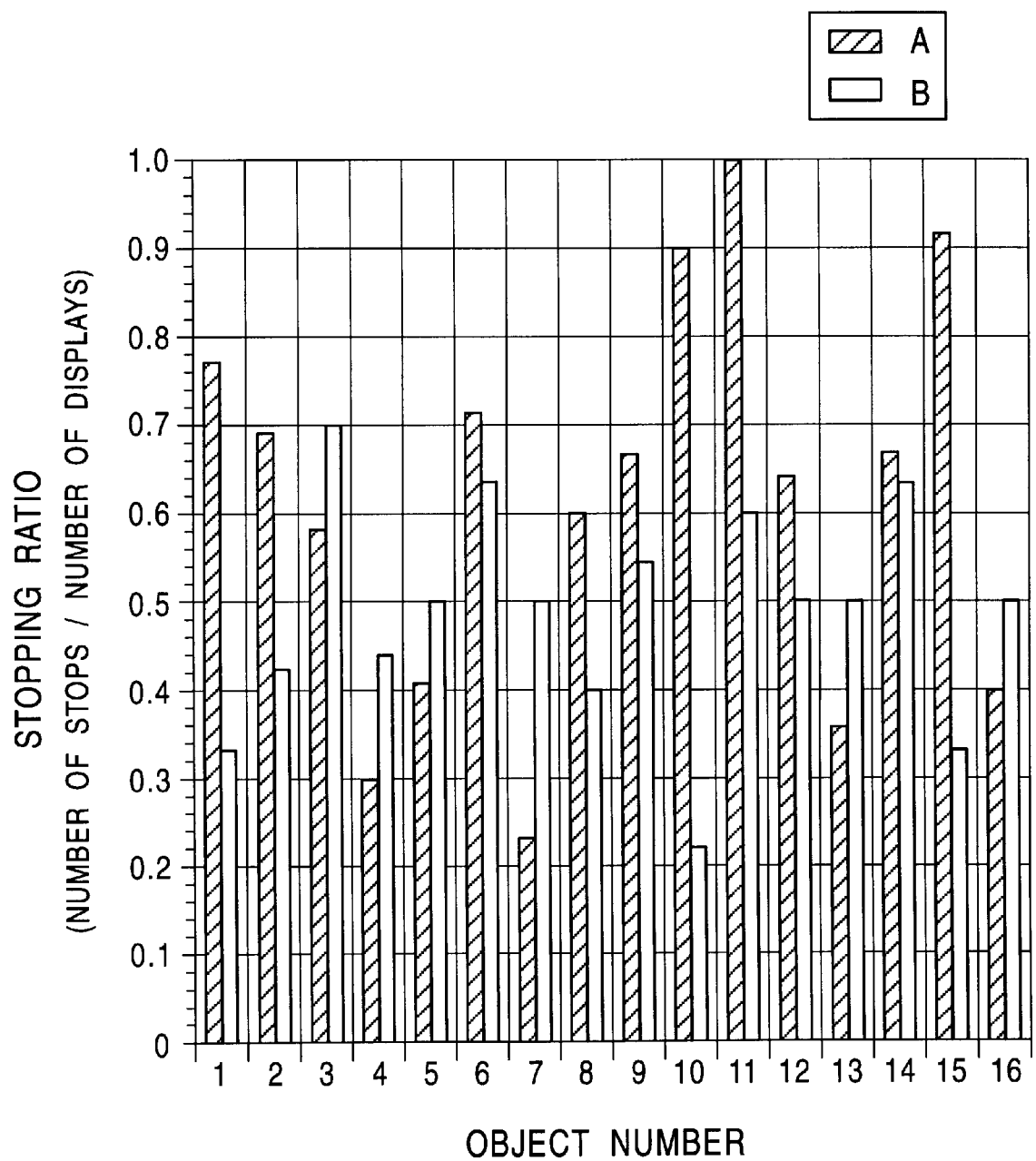
FIG. 14 is a graph showing stopping ratios of focused-on-points while the test subjects are playing the game.

FIG. 14 shows stopping ratios of focused-on-points while the test subjects are playing the game. The horizontal axis represents the numbers of the sixteen objects 1 to 16 displayed in FIGS. 5A to FIG. 8D. The vertical axis represents the stopping ratios. Each stopping ratio is a ratio of the number of times the test subject stopped the focused-on-point at each object to the number of times each object was displayed.

Figure 5A:
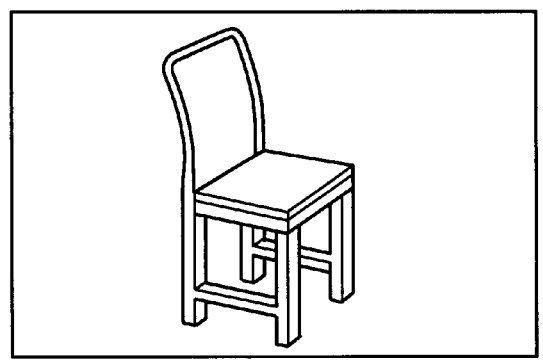
FIGS. 5A to 5D are illustrations of examples of images of inanimate objects.
Figure 5B:
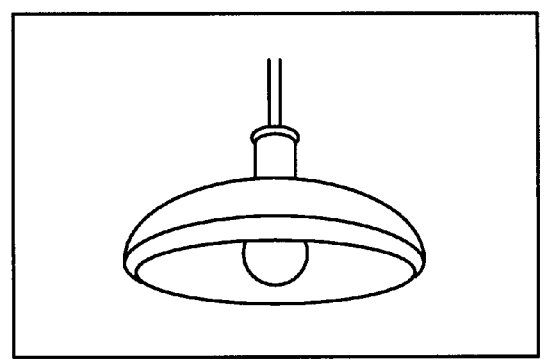
Figure 5C:
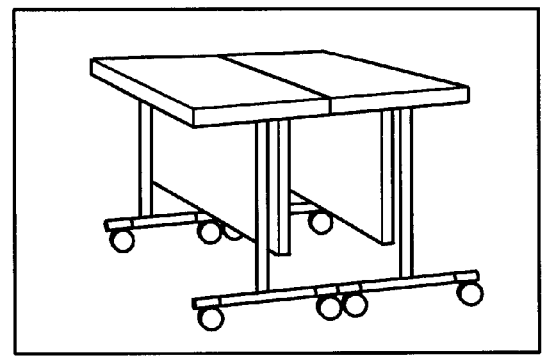
Figure 5D:
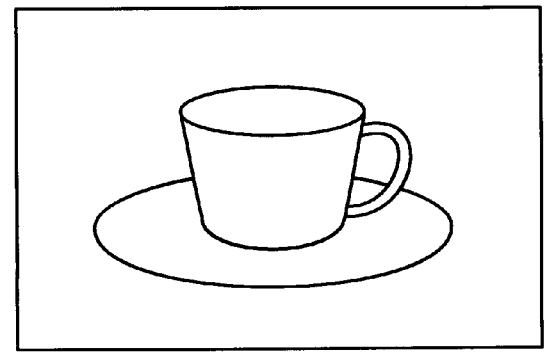
Figure 6A:
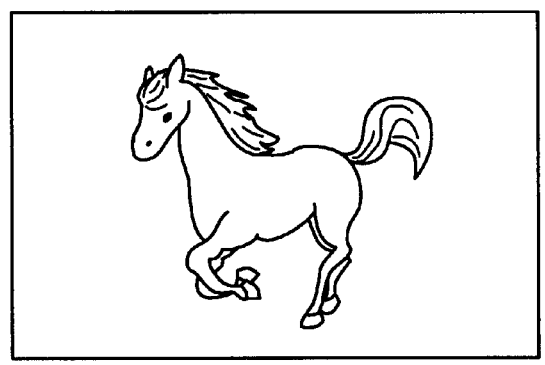
FIGS. 6A to 6D are illustrations of examples of images of animate objects.
Figure 6B:
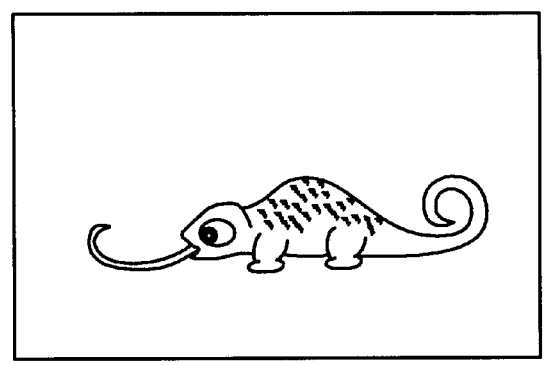
Figure 6C:
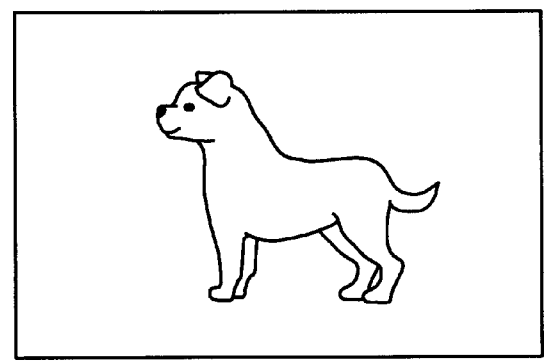
Figure 6D:
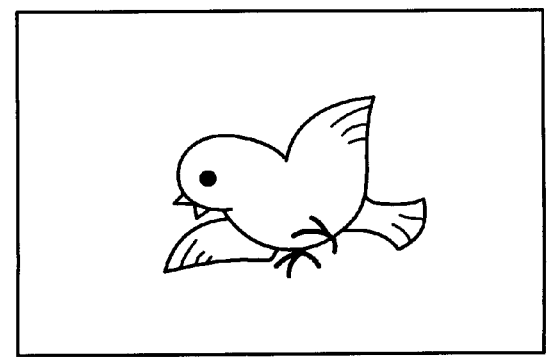
Figure 7A:
FIGS. 7A to 7D are illustrations of examples of images of masks.
Figure 7B:
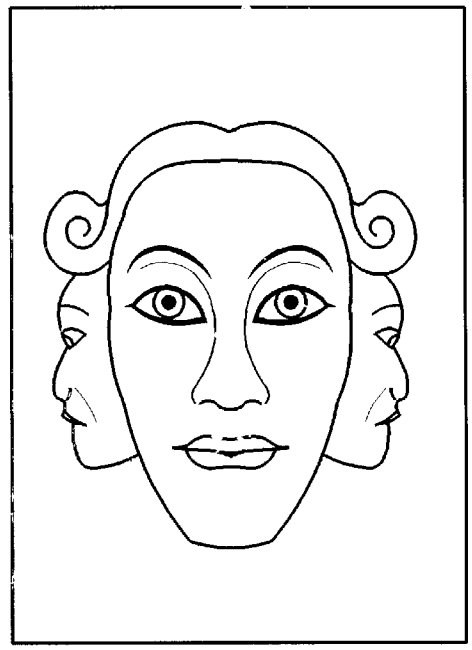
Figure 7C:
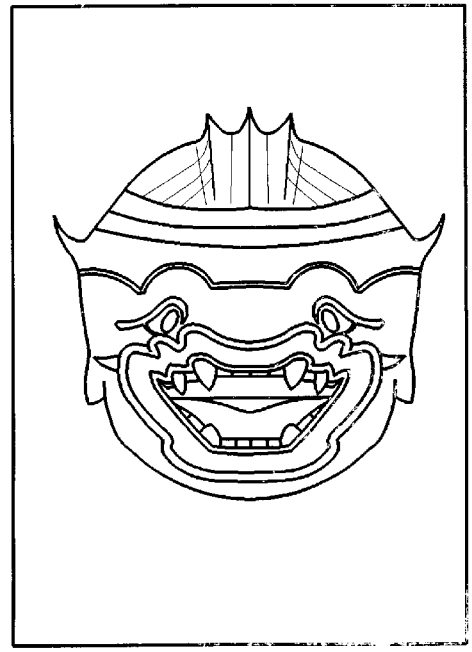
Figure 7D:
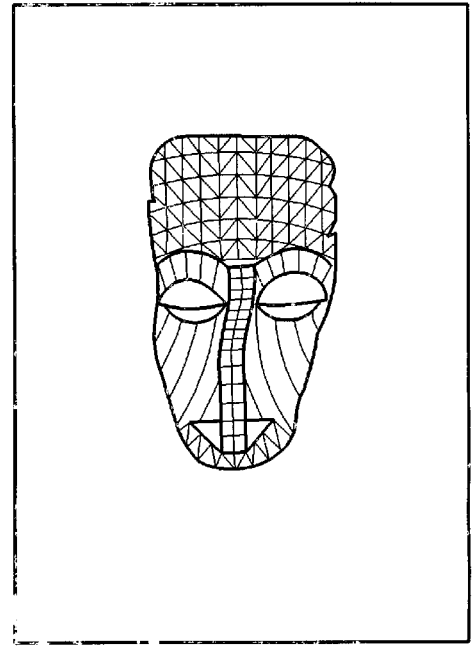
Figure 8A:
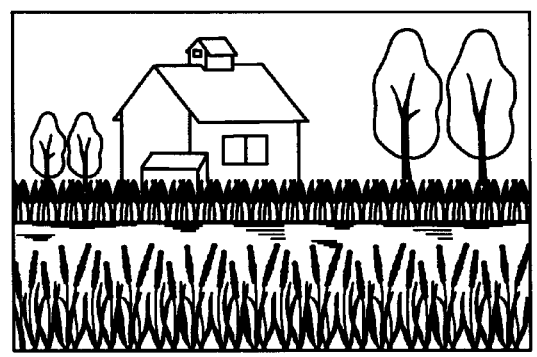
FIGS. 8A to 8D are illustrations of examples of images of landscapes.
Figure 8B:
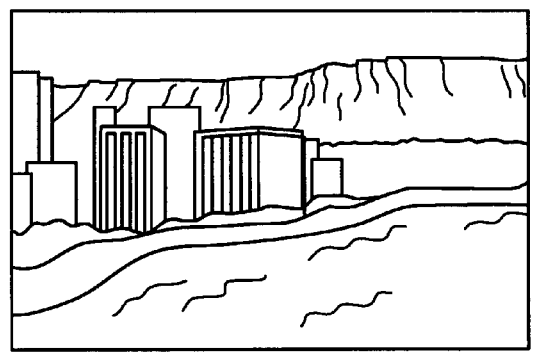
Figure 8C:
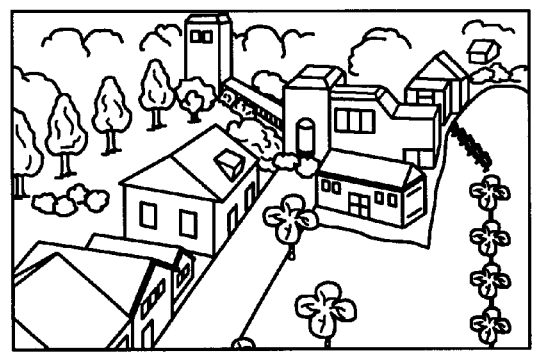
Figure 8D:
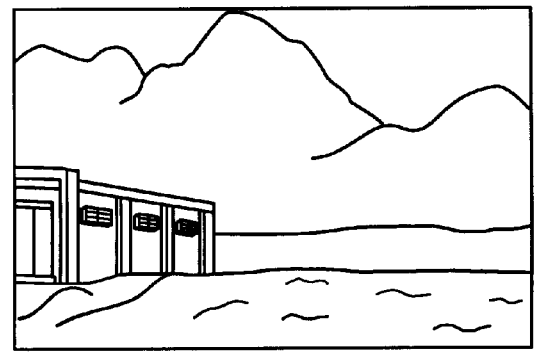

For example, the test subject A has a stopping ratio of approximately 0.77 for the object 1, which is indicated by a cross-hatched bar. This means that when an image of the object 1 shown in FIG. 5A is displayed 100 times, the test subject A will focus the attention 77 times on the image of the object 1. Similarly, the test subject B has a stopping ratio of approximately 0.34 for the object 1, which is indicated by an unshaded bar. This means that when the image of the object 1 is displayed 100 times, the test subject B will focus the attention 34 times on the image of the object 1.

Referring to FIG. 14, it may be concluded that the test subject A has a preference for the objects 10, 11, and 15. However, it is difficult to determine the preference of the test subject A based on FIG. 14 since the stopping ratios for the other objects are relatively high. The test subject B appears to have a preference for the objects 3, 6, 11, and 14. However, it is difficult to reliably determine the preference of the test subject B since the test subject B has a relatively average stopping ratio for each object.

Figure 15:
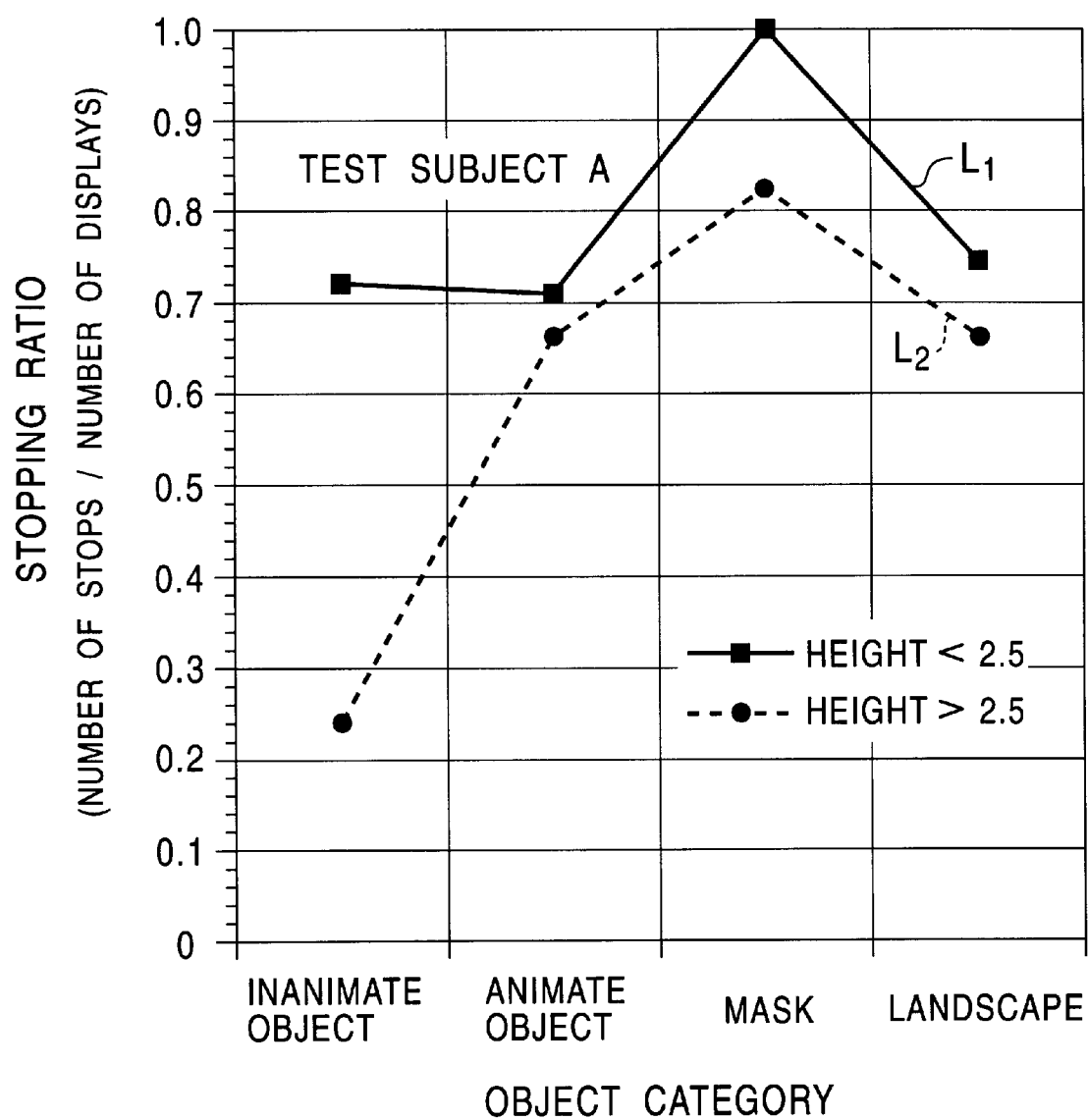
FIG. 15 is a graph showing a variation in the stopping ratios of the test subject A in FIG. 14, based on the height.

FIG. 15 shows two cases of the stopping ratios of the test subject A. One case, indicated by line $L_1$, shows the stopping ratios when the height H is less than 2.5. The other case, indicated by line $L_2$, shows the stopping ratios when the height H is 2.5 or more. In FIG. 15, the stopping ratios are averaged for each object category, i.e., the inanimate object category represented by the objects 1 to 4 (shown in FIGS. 5A to 5D), the animate object category represented by the objects 5 to 8 (shown in FIGS. 6A to 6D), the mask category represented by the objects 9 to 12 (shown in FIGS. 7A to 7D), and the landscape category represented by the objects 13 to 16 (shown in FIGS. 8A to 8D).

As shown in FIG. 15, line $L_1$ has approximately the same stopping ratios for three object categories, i.e., the inanimate objects, the animate objects, and the landscapes, among four object categories, i.e., inanimate objects, animate objects, masks, and landscapes. In contrast, the stopping ratio for the mask category is greater than the stopping ratios for the rest of the object categories. Specifically, the peak of line $L_1$ is the stopping ratio for the masks. Hence, it is possible to determine that the test subject A has a preference for the masks.

In contrast, line $L_2$ has a low stopping ratio for the inanimate objects, and high stopping ratios for the animate objects, the masks, and the landscapes. Based on these results, it may be possible to determine that the test subject A has a preference for the animate objects, the masks, and the landscapes. However, this determination is not very clear since the stopping ratios for the animate objects, the masks, and the landscapes have relatively approximate values.

Line $L_1$ is a graph when the height H is less than 2.5, that is, when the time pressure is high. In contrast, line $L_2$ is a graph when the height H is 2.5 or more, that is, when the time pressure is low. Accordingly, when high time pressure is applied on the test subject, the test subject subconsciously moves the focused-on-point to an image of each object. As a result, the preference of the test subject can be determined in a clearer manner. In other words, the preference can be detected by applying high time pressure on the test subject.

Figure 16:
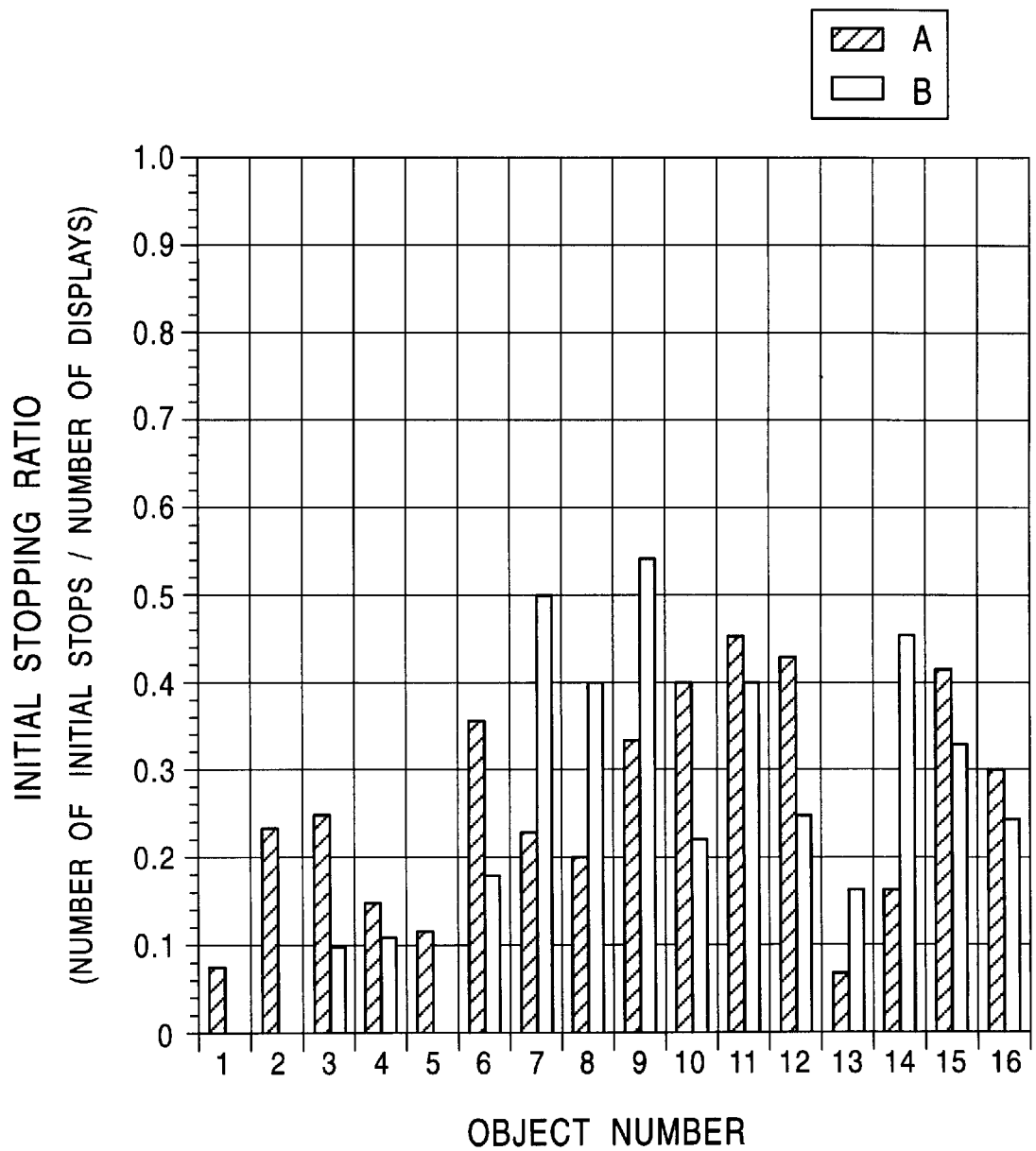
FIG. 16 is a graph showing initial stopping ratios of focused-on-points while the test subjects are playing the game.

FIG. 16 shows initial stopping ratios of focused-on-points while the test subjects are playing the game. The horizontal axis represents the numbers of the objects 1 to 16. The vertical axis represents the initial stopping ratios. Each initial stopping ratio is obtained as follows. When images of plural objects, for example, four objects, are simultaneously displayed, and when the test subject moves the focused-on-point to two of those objects, a ratio is obtained as an initial stopping ratio of the number of stops (initial stops) that the test subject initially made to stop the focused-on-point at each object to the number of displays of each object. For example, the test subject A has an initial stopping ratio of approximately 0.36 for the object 6, which is indicated by a cross-hatched bar. This means that when the object 6 is displayed 100 times, the test subject A will initially focus the attention 36 times at the object 6. Similarly, the test subject B has an initial stopping ratio of approximately 0.18 for the object 6, which is represented by an unshaded bar. This means that when the object 6 is displayed 100 times, the test subject B will initially focus the attention 18 times at the object 6.

It may be impossible to clearly determine the preference of the test subjects A and B based on FIG. 16.

Figure 17:
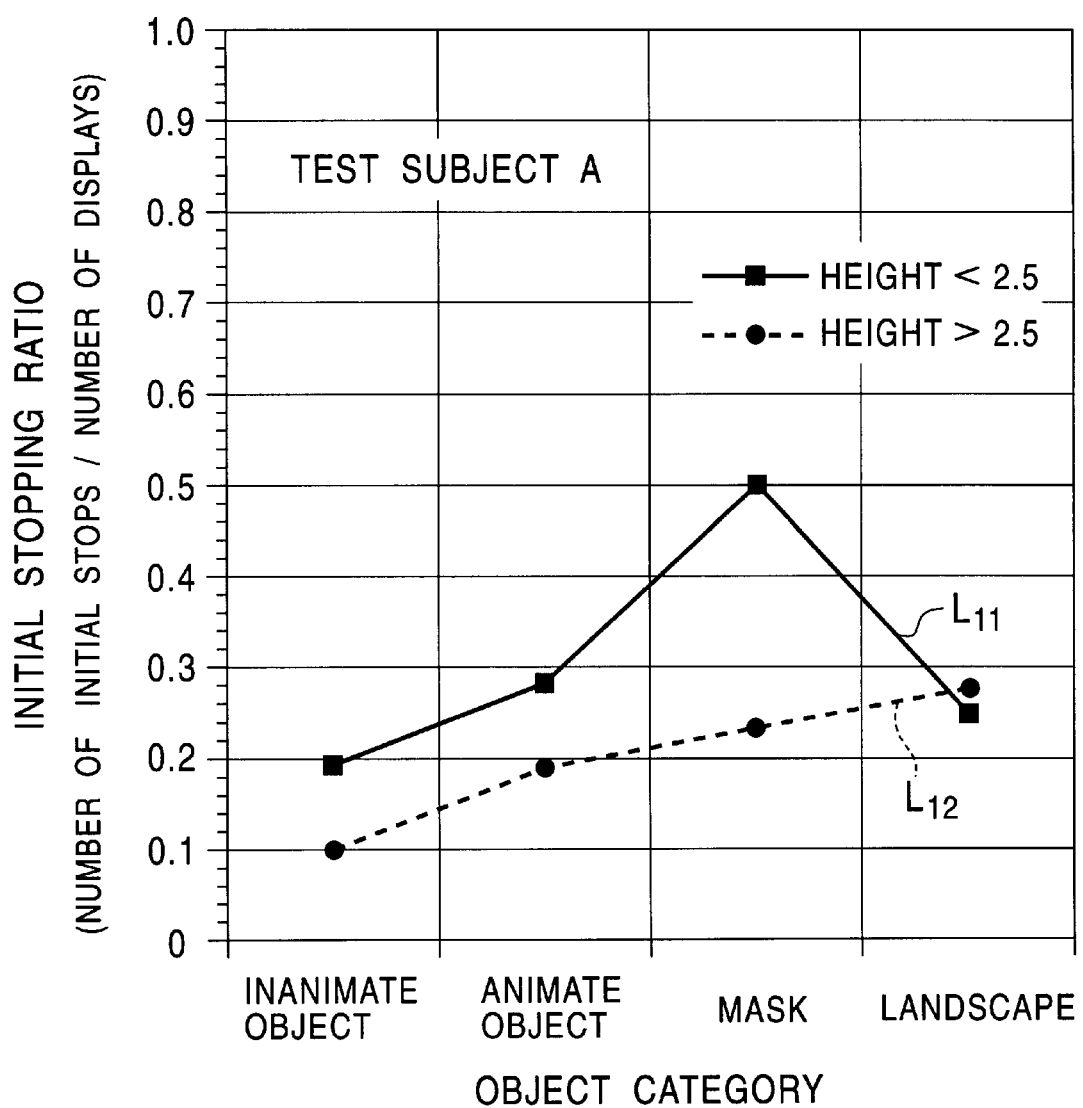
FIG. 17 is a graph showing a variation in the initial stopping ratios of the test subject A in FIG. 16, based on the height.

FIG. 17 shows two cases of the initial stopping ratios of the test subject A. One case, indicated by line $L_{11}$, shows the initial stopping ratios when the height H is less than 2.5. The other case, indicated by line $L_{12}$, shows the initial stopping ratios when the height H is 2.5 or more. As in FIG. 15, the objects on the vertical axis are grouped in four categories.

With continued reference to FIG. 17, line $L_{11}$ representing the case when the height H is less than 2.5, that is, when high time pressure is applied on the test subject A, has approximately the same initial stopping ratios for the inanimate objects, the animate objects, and the landscapes. Line $L_{11}$ shows that the test subject A has a higher initial stopping ratio for the masks. Accordingly, it is clearly determined that the test subject A has a preference for the masks. In contrast, line $L_{12}$ representing the case when the height H is 2.5 or more, that is, when the time pressure is low, has the greatest initial stopping ratio for the landscapes. However, the difference between the initial stopping ratio for the landscapes and the initial stopping ratio for the masks or the animate objects is not very great. Hence, it may be concluded that the test subject A does not have a particular preference for the landscapes.

Accordingly, using the initial stopping ratios permits more reliable detection of the preference of the test subject than using the overall stopping ratios shown in FIG. 15.

Figure 18:
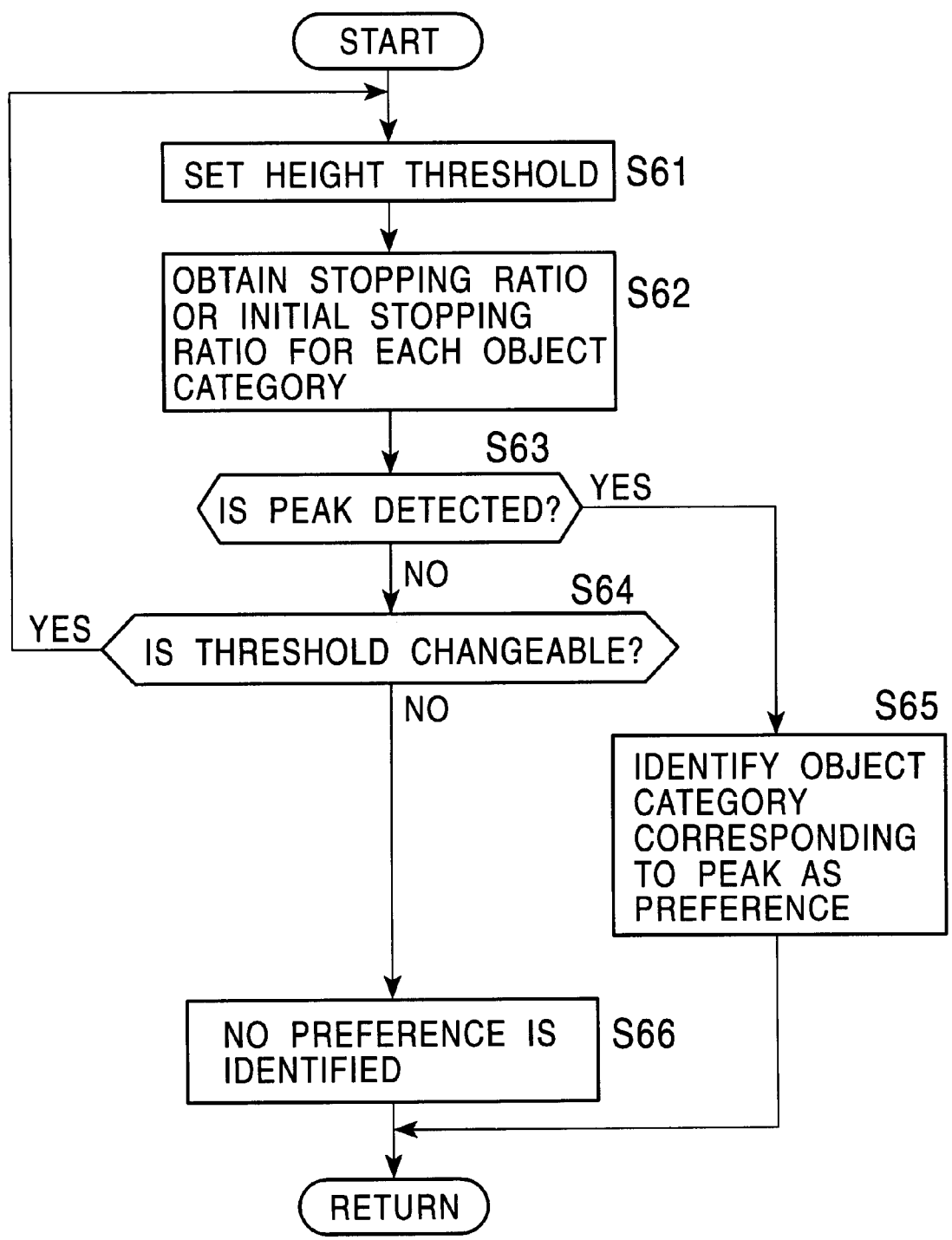
FIG. 18 is a flowchart showing details of step S8 in FIG. 3 for identifying a preference.

Referring now to FIG. 18, the identification unit 8 performs identification processing shown in step S3 in FIG. 3.

In step S61, the identification unit 8 sets predetermined values as height thresholds. As described above, in steps S31 and S32 in FIG. 11, the preference candidate detector 7 detects the object as the preference candidate only when the time pressure is higher than the predetermined threshold. The identification unit 8 initially sets the greatest value (indicating the lowest time pressure) from the set thresholds as an initial threshold.

In step S62, the identification unit 8 obtains the stopping ratio or the initial stopping ratio for each object, as illustrated in FIGS. 15 and 17. In step S63, the identification unit 8 determines whether a peak is detected in the obtained stopping ratio or in the initial stopping ratio. If a peak is not detected, in step S64, the identification unit 8 determines whether the threshold set in step S61 is changeable.

For example, when there is a threshold less than that set in step S61, the threshold can be changed to that smaller value. The identification unit 8 returns to step S61, and changes the threshold to the smaller value. The identification unit 8 performs the above processing. Accordingly, as in the example shown in FIG. 15, line $L_2$ is initially obtained in step S62, and then line $L_1$ is obtained in the subsequent processing. Similarly, as in the example shown in FIG. 17, line $L_{12}$ is initially obtained in step S62, and then line $L_{11}$ is obtained in the subsequent processing.

If the identification unit 8 determines in step S63 that the peak is detected in the stopping ratio or in the initial stopping ratio obtained in step S62, the identification unit 8 identifies in step S65 the object category corresponding to the peak as the preference of the test subject.

If it is determined in step S64 that the threshold is not changeable any more, the identification unit 8 identifies in step S66 that the test subject has no preference. In this case, similar processing is performed after changing the objects to be displayed to the test subject.

The above-described processing may be performed by hardware, or alternatively, may be performed by software. In the latter case, a program in the software can be installed in a computer embedded in specialized hardware, i.e., a preference detecting apparatus, or in a general-purpose personal computer for executing various functions by installing various programs.

Figure 19A:
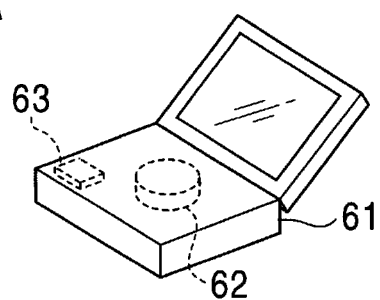
FIGS. 19A to 19C are illustrations of various media.
Figure 19B:
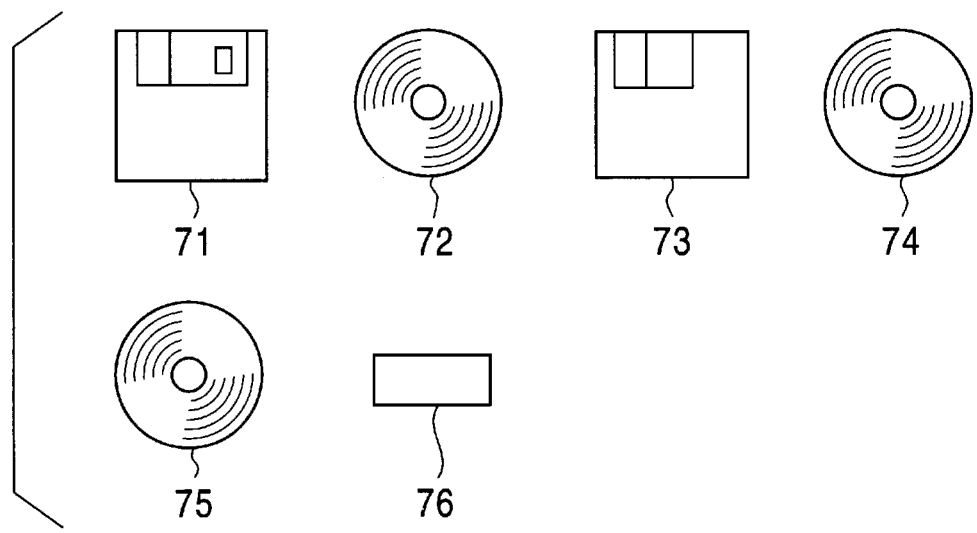
Figure 19C:
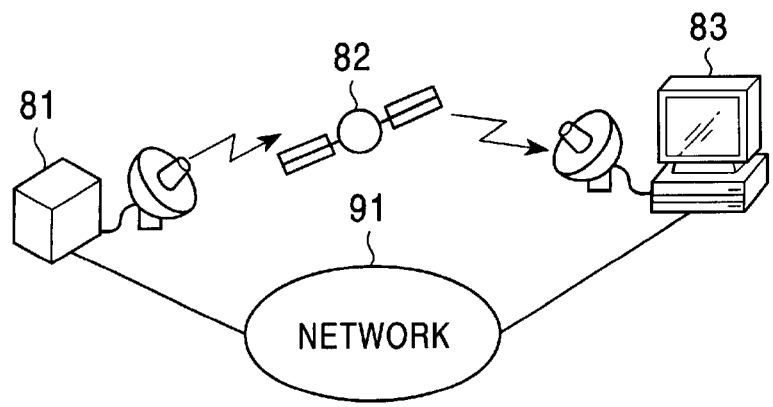

Turning now to FIGS. 19A to 19C, a medium is described for installing the program in a computer for performing the above processing and for causing the computer to execute the program. In this case, the computer is a general-purpose personal computer.

Referring to FIG. 19A, the program may be preinstalled in a built-in recording medium of a personal computer 61, such as a hard disk 62 or a semiconductor memory 63, thus providing a user with the program.

Alternatively, as shown in FIG. 19B, the program may be stored temporarily or permanently in a recording medium, such as a floppy disk 71, a compact disk-read only memory (CD-ROM) 72, a magneto-optical (MO) disk 73, a digital versatile disk (DVD) 74, a magnetic disk 75, or a semiconductor memory 76. Thus, the program can be provided as packaged software.

Referring now to FIG. 19C, the program may be transmitted wirelessly from a download site 81 to a personal computer 83 via a satellite 82 for digital satellite broadcasting. The program may be transmitted by cable to the personal computer 83 via a network 91, such as a local area network or the Internet. The personal computer 83 can store the program in a built-in hard disk.

In this description, the "medium" broadly includes all the above types of media.

In addition to time-series processing following the described order, the process for writing a program provided by the recording medium may also be performed by parallel processing or serial processing.

What is claimed is:

1. A preference detecting apparatus comprising:
   providing means for providing a test subject with predetermined information;
   detecting means for detecting a response of the test subject to the information provided by said providing means;
   applying means for applying time pressure on the response of the test subject to the information provided by said providing means; and
   determining means for determining a preference of the test subject based on a detection result obtained by said detecting means.

2. A preference detecting apparatus according to claim 1, wherein said providing means provides the test subject with images as the predetermined information.

3. A preference detecting apparatus according to claim 2, wherein the images include images classified by category.

4. A preference detecting apparatus according to claim 2, wherein said detecting means detects the response of the test subject based on focusing conditions of the test subject on the images.

5. A preference detecting apparatus according to claim 4, wherein said detecting means detects an image on which attention of the test subject is initially focused.

6. A preference detecting apparatus according to claim 5, wherein said determining means determines the preference of the test subject based on ratios of the images, each ratio being obtained as the number of times the attention of the test subject was focused on each image to the number of times each image was displayed.

7. A preference detecting apparatus according to claim 6, wherein said determining means determines the preference of the test subject based on ratios of the images, each ratio being obtained as the number of times the initial attention of the test subject was focused on each image to the number of times each image was displayed.

8. A preference detecting apparatus according to claim 6, wherein said determining means determines the preference of the test subject based on a peak value of the ratios.

9. A preference detecting apparatus according to claim 8, wherein said determining means detects the peak value of the ratios by changing the time pressure applied by said applying means.

10. A preference detecting apparatus according to claim 1, wherein said applying means includes:
    executing means for causing the test subject to execute a predetermined task; and
    adjusting means for adjusting a period up to completion of the task.

11. A preference detecting apparatus according to claim 10, wherein the task includes a game.

12. A preference detecting method comprising:
    a providing step of providing a test subject with predetermined information;
    a detecting step of detecting a response of the test subject to the information provided by said providing step;

an applying step of applying time pressure on the response of the test subject to the information provided by said providing step; and a determining step of determining a preference of the test subject based on a detection result obtained by said detecting step.

13. A computer-readable medium for causing a computer to execute a program, said program comprising:

a providing step of providing a test subject with predetermined information;

a detecting step of detecting response of the test subject to the information provided by said providing step;

an applying step of applying time pressure on the response of the test subject to the information provided by said providing step; and a determining step of determining a preference of the test subject based on a detection result obtained by said detecting step.

* * * * *